(12) United States Patent
Bimle

(10) Patent No.: US 11,406,789 B2
(45) Date of Patent: Aug. 9, 2022

(54) THERAPY DEVICE AND METHOD OF USE

(71) Applicant: Cynthia Bimle, Ruston, LA (US)

(72) Inventor: Cynthia Bimle, Ruston, LA (US)

(*) Notice: Subject to any disclaimer, the term of this patent is extended or adjusted under 35 U.S.C. 154(b) by 326 days.

(21) Appl. No.: 16/706,673

(22) Filed: Dec. 6, 2019

(65) Prior Publication Data

US 2020/0171270 A1 Jun. 4, 2020

Related U.S. Application Data

(60) Provisional application No. 62/774,005, filed on Nov. 30, 2018.

(51) Int. Cl.
*A61M 21/02* (2006.01)
*A61M 21/00* (2006.01)

(52) U.S. Cl.
CPC ..... *A61M 21/02* (2013.01); *A61M 2021/0016* (2013.01); *A61M 2205/123* (2013.01); *A61M 2205/3303* (2013.01); *A61M 2205/59* (2013.01); *A61M 2209/088* (2013.01)

(58) Field of Classification Search
CPC .......... A61M 21/02; A61M 2021/0016; A61M 2205/123; A61M 2205/3303; A61M 2205/59; A61M 2209/088; A61M 15/08; A61M 2021/0022; A61M 2021/0027; A61M 2021/0044; A61M 2205/3553; A61M 2205/8256; A44C 15/002
USPC ....................................................... 600/26–28
See application file for complete search history.

(56) References Cited

U.S. PATENT DOCUMENTS

| 9,125,461 | B2 | 9/2015 | Liberman et al. | |
|---|---|---|---|---|
| 2004/0096603 | A1* | 5/2004 | Enguchi | A44C 15/002 428/34.1 |
| 2006/0062408 | A1* | 3/2006 | Cho | H04M 1/21 381/177 |

(Continued)

FOREIGN PATENT DOCUMENTS

| CN | 107549941 B1 | 1/2018 |
|---|---|---|
| CN | 109123938 B1 | 10/2018 |

(Continued)

OTHER PUBLICATIONS

Daniels JK, Vermetten E. Odor-induced recall of emotional memories in PTSD-Review and new paradigm for research. Exp Neurol. Oct. 2016;284(Pt B):168-180. doi: 10.1016/j.expneurol.2016.08. 001. Epub Aug. 7, 2016. PMID: 27511295. (Year: 2016).*

*Primary Examiner* — Sunita Reddy
(74) *Attorney, Agent, or Firm* — Melissa Dobson; Hoffman Warnick LLC

(57) ABSTRACT

The therapy device disclosed is structured and configured to be a wearable device self-controlled, remote controlled by a caregiver, and/or integrated with a downloadable application (app) from a mobile device to assist a caregiver with modifying and enforcing behaviors as aligned with olfactory sensation and personalized limbic system functionality. The device and system may also be configured and combined with another therapeutic device or medical monitoring system such that the therapy device disclosed herein is aligned to initiate when a target or monitored condition reaches a threshold value. Such configurations would allow the device to function automatically and in combination with data analytics.

19 Claims, 3 Drawing Sheets

(56) References Cited

U.S. PATENT DOCUMENTS

| | | | | |
|---|---|---|---|---|
| 2008/0164339 | A1* | 7/2008 | Duru | B05B 17/0676 |
| | | | | 239/102.2 |
| 2009/0012433 | A1* | 1/2009 | Fernstrom | A61B 5/0022 |
| | | | | 600/593 |
| 2016/0080855 | A1* | 3/2016 | Greenberg | H04R 1/028 |
| | | | | 381/74 |
| 2017/0012925 | A1* | 1/2017 | Tekin | H04L 51/32 |
| 2017/0354231 | A1* | 12/2017 | Okumura | B05B 12/02 |
| 2021/0213237 | A1* | 7/2021 | Kelsen | A61M 21/00 |
| 2021/0283627 | A1* | 9/2021 | Andrinal Lopez | A61M 11/00 |

FOREIGN PATENT DOCUMENTS

| | | |
|---|---|---|
| CN | 108851401 B1 | 11/2018 |
| KR | 2008025856 B1 | 3/2008 |
| KR | 2017026928 B1 | 3/2017 |
| KR | 2017026930 B1 | 3/2017 |
| KR | 2017100873 B1 | 9/2017 |

\* cited by examiner

THERAPY DEVICE AND METHOD OF USE

PRIORITY CLAIM

The present application claims priority to Provisional Application No. 62/774,005, filed Nov. 30, 2018, and titled Que.

FIELD OF THE INVENTION

The present invention relates generally to therapy devices, and more particularly, relates to utilizing the sense of smell as it integrates with the limbic system of the brain and functionality of neural pathways.

BACKGROUND OF THE INVENTION

Attention deficit hyperactivity disorder (ADHD) is a mental disorder of the neurodevelopmental type. It is characterized by problems paying attention, excessive activity, or difficulty controlling a behavior which is not appropriate for a person's age. The symptoms appear before a person is twelve years old, present for more than six months, and cause problems in at least two settings (such as school, home, or recreational activities). In children, problems paying attention may result in poor school performance. Additionally, ADHD is typically associated with other mental disorders and substance misuse. Although ADHD causes impairment, particularly in modern society, many children with ADHD have a good attention span for tasks of interest.

Current processes in treating children with ADHD include prescription medication or therapy targeted at disciplining children's behavior(s). The prescription prices rise every year and alternative therapy prices escalate when special attention is needed for a particular child. Similarly, this relates with special needs children, those with other neural and mental disorders and conditions.

A need exists for a device that will eliminate any sort of medication and that will instantly change a behavior to improve learning and better address behaviors without harsh methodology. Various attempts have been made to solve the problems addressed above which may be found in the prior art but have thus far been unsuccessful. A need exists for a reliable methodology and system to avoid and better address mental and behavioral issues to which research, medical diagnoses and treatments have lacked understanding.

It is therefore resolved to overcome the aforementioned problems and shortcomings of the prior art that the present disclosure is embodied.

SUMMARY OF THE INVENTION

In view of the foregoing disadvantages inherent in the known art, the present invention provides a novel therapy device, system and method of use. The general purpose of embodiments disclosed herein, which will be subsequently described in greater detail, is to provide an aroma therapy necklace structured and arranged to utilize one's strong sense of smell to subtly reinforce a behavior in a positive or negative way by emitting a fine mist of a pleasant or offensive smell to encourage the wearer to respond in a positive way or to extinguish negative behavior.

The features of embodiments disclosed herein are distinguished and identified in the following specification. These and other features, aspects, and advantages of the disclosed novelty will become better understood with reference to the following drawings and detailed descriptions.

The therapy device and system utilizes the sense of smell to integrate with the limbic system of the brain and functionality of neural pathways, using the scent to cue particular realized behaviors of a person.

One's sense of smell is the only one of the human identified senses that route to the limbic system of the brain. Specifically, the limbic system of the brain supports a variety of functions including memory, emotion, behavior, motivation, and olfaction. Emotional life is largely housed in the limbic system, and critically aids the formation of memories. With a primordial structure, the limbic system is involved in lower order emotional processing of input from sensory systems. As such, various disorders and human conditions may be resolved or curtailed by targeting olfactory sensation and neural processing of such cues. For exemplary purposes, and not limitation, military persons with depression and post-traumatic stress disorder may be targeted populations for the embodied therapeutic device and system. The therapist could incorporate the therapeutic device with the designed therapy and teach a person to utilize the device alone, or in combination with an app accessible via mobile communications to initiate a positive cue such as a scent that is personalized and preconditioned to the designated patient to be associated with a positive thought. The therapeutic device in this circumstance would permit the patient to go to his/her personalized happy place in mind. The smell preconditioned to the positive cue will assist a patient in getting to the happy place quicker and easier. Instead of reaching of a cigarette or another crutch in stress or emotional circumstance, the therapeutic device would offer an alternative to individually condition the mind, a new form of personalized medicine.

In another aspect, the therapeutic device could be programmed when a person's heart rate elevates above a particular threshold in anxiety or fear, or when heart rate drops such as when one might fall asleep at the wheel. Variations of the device provide therapeutic conditional of neural response and personalized stimuli or depressants to improve brain health.

Various embodiments can be modified in size, shape, dimension, materials utilized, as well as adding automated and/or electronic configurations. In one aspect, an embodiment is personalized to a patient who is monitoring his blood pressure. The app is downloaded to a mobile device or to the wearable therapy device and integrated with the release or aromatherapy directed scents personalized to the patient's limbic system. Such implementations and modifications are apparent by one skilled in the art.

For exemplary purposes, and not limitation, varying uses and aspects may be employed for use with individuals, populations of individuals and groups, individually or in combination, to include infants, children, adults, and the aging population, among other variations across species.

BRIEF DESCRIPTION OF THE DRAWINGS

The accompanying drawings, which are incorporated in and constitute a part of this specification, illustrate various embodiments of the present invention, and, together with the description, serve to explain the principles of the invention. The various features are not necessarily drawn to scale. In fact, the dimensions may be arbitrarily increased or decreased for clarity of discussion. In the drawings.

The various embodiments will hereinafter be described in conjunction with the appended drawings.

DETAILED DESCRIPTION

Reference will now be made in detail to the present embodiments of the invention, examples of which are illustrated in the accompanying drawings. Wherever possible, the same reference numbers will be used throughout the drawings to refer to the same or like parts.

Embodiments of the present invention relate to a therapy device, particularly to a wearable therapeutic device such as jewelry, and more directly to an aromatherapy device structured and arranged to utilize and cue one's sense of smell to subtly reinforce a behavior in a positive or negative way. By emitting a fine mist of a pleasant or offensive smell, as personalized to an individual or patient, the wearer of the device is encouraged to respond in a positive way or extinguish negative behavior.

Figure 1:
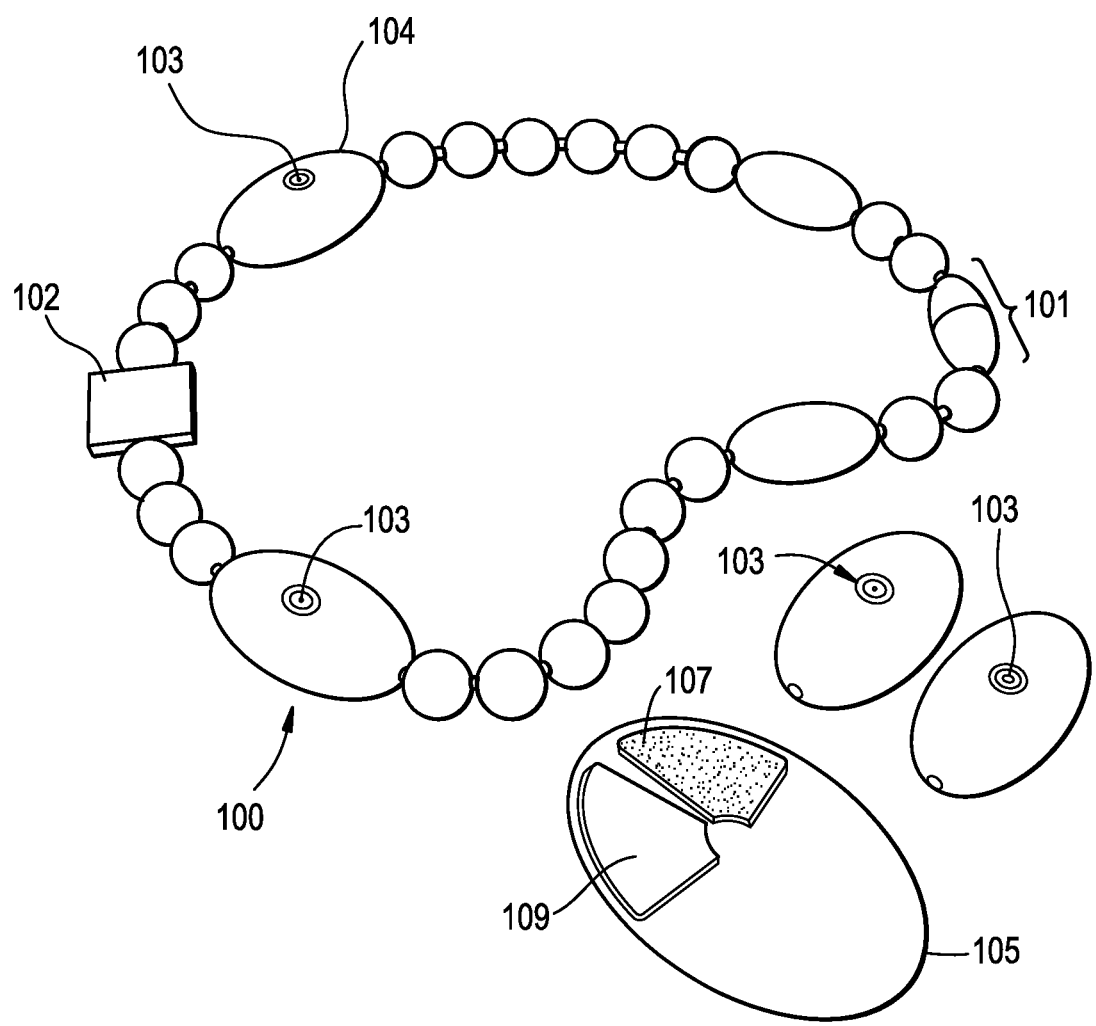
FIG. 1 is a perspective view of an embodiment of the system.
Figure 2:
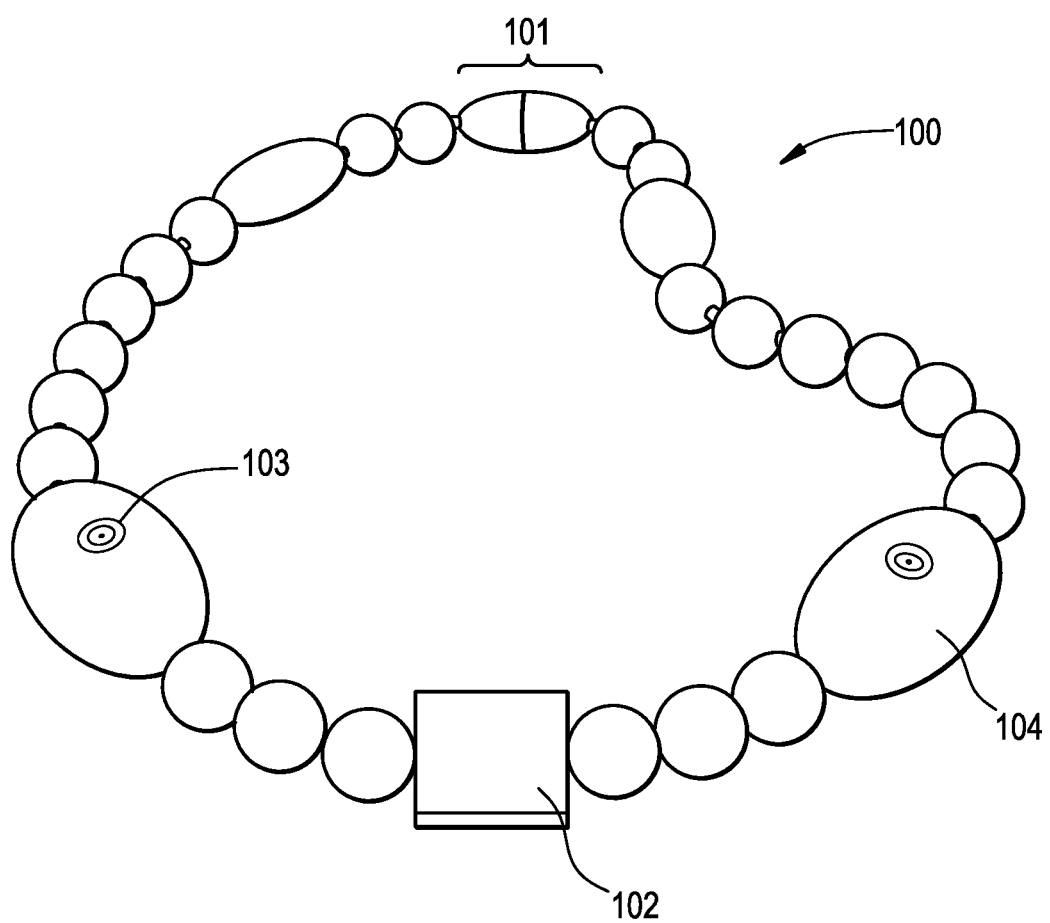
FIG. 2 is another perspective view of an embodiment.
Figure 3:
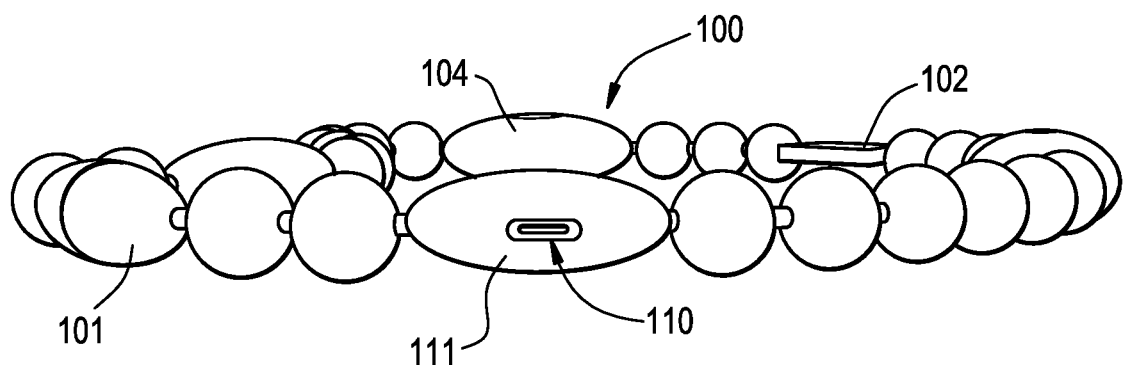
FIG. 3 is a perspective view of one embodiment of the device.
Figure 4:
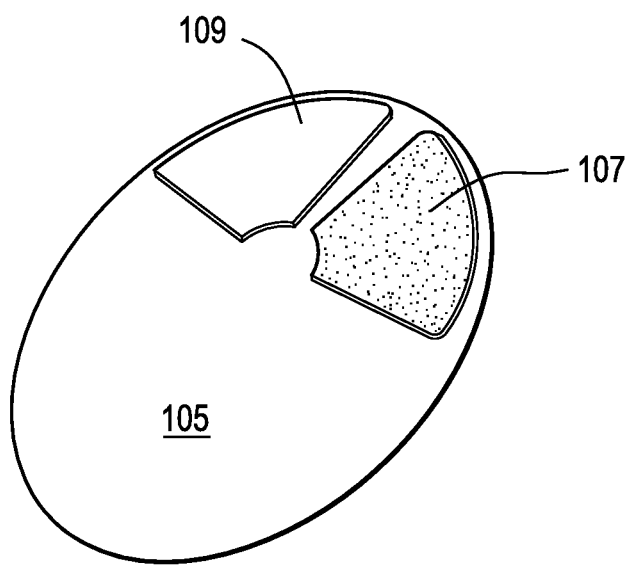
FIG. 4 is a perspective view of a component of the system in one embodiment.

Referring to the drawings of FIG. 1-5, the therapy device 100 is a therapy necklace 100 connected by way of a screw cap 101 or other clasp and designed to emit certain smells that will direct the behavior of children with ADHD or with special needs. The therapy device takes the form of a wearable necklace 100. The therapy device holds two or more hollow beads that are filled with fragrance as loaded through a dispenser 103 into a first bead 102 with a pleasant fragrance and a second bead 104 with an unpleasant fragrance. With a press of a button on a remote device 105, a therapist or caretaker will be able to speak to the child with ADHD (indirectly via the olfactory communications or directly through a microphone/speaker) and teach them how to behave correctly, or as desired, with the fragrances.

Aspects of the embodiments disclosed herein allow components of the device to be refillable, personalized and selected fragrances aligned with behavior therapy or other therapy, durable and wearable devices, rigid and/or malleable configurations, rechargeable where electronics are employed, offering an app for a therapist/teacher to control and direct multiple patients/individuals, easy-to-use remote paired with each device, screw cap or snap on cap with safety seal to prevent fragrance removal, or safety designs to prevent hazardous wearables, edible and biodegradable reusables and fragrances, ability to be sanitized and cleaned, adjustable mist or fragrance release controls, and in combination with any design, fashion or otherwise to include logos, branding and marking. The benefits and advantages listed are for exemplary purposes and not limitation.

The therapy device 100 may be shaped in various forms, including round beads such as the second bead 104, and/or a large square pendant as shown by a first bead 102, among others. If the child with ADHD begins to lose focus, the therapy device 100 may include other sensory indicators and sensations such as to be less rigid and malleable for squeezing and safe for biting when the child feels anxious. The remote control 105 may have two or more buttons, each of which initiates the release of the fragrance of the respective two or more beads.

In one aspect, the first bead and the second bead are preloaded with specified scents, one personalized to reward behavior, and the other to curtail, adjust, or modify behavior, the buttons on the remote 105 aligned with the positive behavior stimulus control 107 and the negative stimulus control 109. Various numbers of beads, configurations, sizes and shapes may be employed as based on severity of behavior, as age appropriate, or as directed to a particular disease, condition, or diagnosis. Where the therapy device 100 implements a remote or other electronics, the charging port 110 is implemented in a bead or component 111 of the device 100.

In another aspect, the beads are refillable to allow consumers to fill essential oils or various scented solutions of choice as desired into the therapy device component beads. As referenced here, component beads may be configurations that can contain the aroma or fragrance in solid, liquid, or modified state. Immediately upon the initiation of a positive behavior or taught response, the teacher or therapist rewards the conduct with a pleasurable smell. An incorrect or unwanted behavior can be punished with a noxious smell. The features can be presented in various forms and in a variety of therapeutic methodologies to engage the limbic system and neural functionalities. Such features create new processes to treat children with ADHD, children with special needs, patients with autism and on the autism spectrum, patients with depression, mental and/or behavioral disorders, among others. Any pathway that ties to the neural system could potentially line up with use of the disclosed olfactory therapeutic device.

In one aspect, the unique features of the device provide benefits for a variety of individuals and patients everywhere. The device will awaken the child's sense of smell while cueing the child to return their focus back into school work or therapy sessions. The device will also distract or stop an uncooperative autistic or special needs child without using force or loud words. Medication and prescription pills or lengthy therapy and excessive costs may also be reduced significantly such that parent and teachers can better direct behaviors of children and students, respectively. As well, the device offers a minimally invasive treatment option that is cost effective and economically available across populations.

Since one's smell is personalized to an individual and directed in combination with the limbic system of the brain, scent directs functionality of a person's brain as it controls and power memory, emotion, behavior, motivation, and olfaction. Emotional life, response and aligned behaviors result from the respective stimulation and response of the limbic system. As such, various disorders and human conditions may be resolved or curtailed by targeting olfactory senses, sensation and neural processing of such cues. For exemplary purposes, and not limitation, military persons with depression and post-traumatic stress disorder may be targeted populations for the embodied therapeutic device and system. Seniors with aging dementia may also be treated for conditions and mental health associated with Alzheimer's. The therapist could incorporate the therapeutic device with the personalized designed therapy for a patient and teach a person to utilize the device alone, or in combination with an app accessible via mobile communications to initiate a positive cue such as a scent that is personalized and preconditioned to the designated patient to be associated with a positive thought. The therapeutic device in this circumstance would permit the patient to go to his/her personalized happy place in mind. The smell preconditioned to the positive cue will assist a patient in getting to the happy place quicker and easier. Instead of reaching of a cigarette or another crutch in stress or emotional circumstance, the therapeutic device would offer an alternative to individually condition the mind, a new form of personalized medicine.

In another aspect, the therapeutic device could be programmed when a person's heart rate elevates above a particular threshold in anxiety or fear, or when heart rate drops such as when one might fall asleep at the wheel. Variations of the device provide therapeutic treatments to a variety of individuals having mental conditions or disorders, behavioral needs, among others. Providers such as therapists, physicians and medical staff, as well as teachers, parents, and caregivers would have access to minimally invasive treatments that offer positive and negative reinforcement as well as feedback loops, allowing the collection of data and integration of data analytics where the device integrates electronics and data systems.

Any modification of information or use of the above may include any number of variables be implemented and modified to achieve the same and does not depart from the spirit and scope of the disclosed invention. Such variables may include sizes, shapes, dimensions, compositions or otherwise, not to depart from aspects of the invention.

The therapy device, system, and method of use utilizes the sense of smell to integrate with the limbic system of the brain and functionality of neural pathways, using the scent to cue particular realized behaviors of a person. In one embodiment, a person's olfactory senses are tested in a screening to determine personalized preferences of likes, dislikes, neutral reactions and/or behaviors. In a next step, the person has a personalized device constructed with positive and negative and/or neutral fragrances. The personalized device may encompass stimulants for other senses including visual, auditory, touch, taste, and olfactory, the touch being squeezable, soft, textured, and any number of encompassing designs as stimuli or deterrents to trigger behaviors and attitudes/moods. The personalized device may be a wearable in the form of jewelry, an attachable item or device, or be integrated with another medical device such as a blood pressure or heart rate monitor. When the patient or individual feels anxiety or stress, the individual may trigger the stimulus or sensation such as positive scent. In another aspect, if the therapy is incorporated or integral with the medical device, the stimuli may be released automatically as set by a personalized threshold and regulated and determined by the caregiver. In another aspect, when a caregiver is monitoring behavior, and a patient acts in a violent or severe manner to cause harm to him/herself, the caregiver will be capable of activating the therapy device with the desired olfactory scent or other choosing. The remote may be in the form of a simple button control or implemented as an app on a phone or mobile device. Variations of controls and regulation of the therapy device and methods of use may be modified as utilized and incorporated in specified conditions and specialized treatments.

In the embodiment disclosed herein, the device is a wearable necklace 100. The device may be implemented with military IDs or dogtags, identification tags in private or public settings, as wristlets, malleable toys or stress balls, among others.

The embodiments of the invention described herein are exemplary and numerous modifications, variations, and rearrangements can be readily envisioned to achieve substantially equivalent results, all of which are intended to be embraced within the spirit and scope of the invention. Further, the disclosure herein enables one of skill in the art to practice and modify the embodiments disclosed without departing from the scope and essence of the disclosed device, system, and method of use.

What is claimed is:

1. A portable therapeutic olfactory device comprising:
   a first component including a first olfactory feature disposed within, the first olfactory feature capable of being refilled or replaced with a first consumable;
   a second component including a second olfactory feature disposed within, the second olfactory feature capable of being refilled or replaced as a second, different consumable;
   wherein the first component includes a first dispenser to diffuse the first consumable and the second component includes a second dispenser to diffuse the second consumable;
   a third component connected to the first component and the second component, the third component comprising a charging port disposed within; and
   an electronic control unit configured to communicate with the first component and the second component such that the control unit activates the first olfactory feature when a first response is desired and activates the second olfactory feature when a second, different response is desired;
   wherein the first olfactory feature and the second olfactory feature are personalized to an individual's limbic system to promote personal physical and mental health of the individual, and
   wherein the device is in a wearable form comprising a necklace or a wrist wearable, and wherein each of the first component, the second component, and the third component is a bead connected to each other in the device in the wearable form.

2. The device of claim 1, wherein the first component and the second component are integrated with a medical monitoring device.

3. A method of using the device of claim 1, the method comprising:
   providing the portable therapeutic olfactory device;
   screening the individual for personalized preferences to one or more olfactory features;
   assembling the portable therapeutic olfactory device having the first olfactory feature and the second olfactory feature according to the personalized preferences of the individual;
   integrating the portable therapeutic olfactory device within an environment of the individual in wearable configuration or in proximity to the individual;
   providing the control unit to remotely control a release of the first olfactory feature and the second olfactory feature.

4. The method of claim 3, wherein the screening further comprises testing the individual to determine personalized preferences of likes, dislikes, neutral reactions and behaviors.

5. The method of claim 3, wherein the personalized preferences include a personalized sensory preference including olfactory, visual, auditory, touch, or taste sense.

6. The method of claim 3, wherein the step of providing the portable therapeutic olfactory device includes providing the portable therapeutic olfactory device in a personalized wearable form customized to an individual's condition.

7. The method of claim 6, wherein the individual's condition is a mental health condition.

8. The method of claim 6, wherein the individual's condition comprises attention deficit hyperactivity disorder (ADHD), autism, post-traumatic stress disorder (PTSD), anxiety, or stress.

9. The device of claim 1, wherein the control unit is remotely accessible.

10. The device of claim 1, further comprising an application via a mobile device to monitor and control the control unit.

11. The device of claim 1, wherein the device is a personalized device to stimulate senses comprising visual, auditory, touch, or taste.

12. The device of claim 11, wherein the personalized device comprises a stimulus or a deterrent to trigger one or more of behaviors, attitudes, and moods of the individual.

13. The device of claim 1, where the wearable form further comprises a jewelry, an identification tag, a malleable toy, or a stress balls.

14. The device of claim 1, wherein the electronic control unit further includes a mechanical unit.

15. An aromatherapy system to treat a mental health condition, the system comprising:
- a first component including a first olfactory feature disposed within, the first olfactory feature capable of being refilled or replaced with a first consumable;
- a second component including a second olfactory feature disposed within, the second olfactory feature capable of being refilled or replaced as a second, different consumable;
- wherein the first component includes a first dispenser to diffuse the first consumable and the second component includes a second dispenser to diffuse the second consumable;
- a third component connected to the first component and the second component, the third component comprising a charging port disposed within,
- wherein each of the first component, the second component, and the third component is a bead connected to each other in a portable device in a wearable form that comprises a necklace or a wrist wearable;
- an electronic control unit configured to communicate with the first component and the second component such that the control unit activates the first olfactory feature when a first response is desired and activates the second olfactory feature when a second, different response is desired,
- wherein the first olfactory feature and the second olfactory feature are personalized to an individual's limbic system to promote personal physical and mental health of the individual; and
- a data capture module and display to integrate with an app to track and monitor a function of the individual's limbic system.

16. The system of claim 15, wherein the first component and the second component are integrated in a wearable device or as an attachable item.

17. The system of claim 15, wherein one or both of the first component and the second component are integrated with a medical device.

18. The system of claim 17, wherein the medical device is a medical monitoring device.

19. The system of claim 15, wherein the electronic control unit further includes a mechanical unit.

* * * * *